(12) United States Patent
Kloth et al.

(10) Patent No.: US 9,878,963 B2
(45) Date of Patent: Jan. 30, 2018

(54) PROCESS FOR THE PREPARATION OF AN OLEFINIC PRODUCT FROM AN OXYGENATE

(71) Applicant: SHELL OIL COMPANY, Houston, TX (US)

(72) Inventors: Antonius Gijsbertus Johannes Kloth, Vaals (NL); Sivakumar Sadasivan Vijayakumari, Gonzales, LA (US); Jeroen Van Westrenen, Amsterdam (NL)

( * ) Notice: Subject to any disclaimer, the term of this patent is extended or adjusted under 35 U.S.C. 154(b) by 36 days.

(21) Appl. No.: 14/655,345

(22) PCT Filed: Dec. 24, 2013

(86) PCT No.: PCT/EP2013/077996
§ 371 (c)(1),
(2) Date: Jun. 25, 2015

(87) PCT Pub. No.: WO2014/102284
PCT Pub. Date: Jul. 3, 2014

(65) Prior Publication Data
US 2015/0353440 A1    Dec. 10, 2015

(30) Foreign Application Priority Data

Dec. 28, 2012 (EP) .................................. 12199591

(51) Int. Cl.
*C07C 1/20* (2006.01)
*C07C 7/00* (2006.01)
(52) U.S. Cl.
CPC .............. *C07C 1/20* (2013.01); *C07C 7/005* (2013.01); *C07C 2529/00* (2013.01); *Y02P 30/42* (2015.11); *Y02P 30/48* (2015.11)

(58) Field of Classification Search
CPC ................. C07C 1/00; C07C 1/20; C07C 4/06
USPC ........ 585/638, 639, 640, 641, 648, 800, 809, 585/330, 300, 301, 310; 62/121
See application file for complete search history.

(56) References Cited

U.S. PATENT DOCUMENTS

| | | | |
|---|---|---|---|
| 7,214,843 B2 * | 5/2007 | Beech, Jr. ................ | C07C 1/20 585/638 |
| 2005/0038304 A1 * | 2/2005 | Van Egmond ........... | C07C 1/20 585/324 |
| 2007/0203382 A1 | 8/2007 | Senetar | |

FOREIGN PATENT DOCUMENTS

| | | |
|---|---|---|
| CN | 102675019 | 9/2012 |
| CN | 102746083 A | 10/2012 |
| CN | 102704683 | 5/2015 |
| WO | 2008039552 | 4/2008 |

* cited by examiner

*Primary Examiner* — Sharon Pregler

(57) ABSTRACT

The invention relates to process for the preparation of an olefinic product comprising ethylene and/or propylene from an oxygenate, the process comprising the following steps: a) an oxygenate conversion step wherein a gaseous effluent comprising olefins and a water-soluble oxygenate is obtained; b) separation of water from the effluent; c) compression of the effluent; d) acid gas removal from the compressed gaseous effluent obtained in step c), wherein the compressed gaseous effluent is treated with a caustic solution in a caustic tower; and e) separating the olefinic product from the gaseous effluent treated in step d), wherein, in a final stage in the caustic tower, water-depleted compressed gaseous effluent is treated with a water stream that is essentially free of water-soluble oxygenate and a spent water stream comprising caustic and water-soluble oxygenate is obtained, which spent water stream is withdrawn from the process.

9 Claims, 1 Drawing Sheet

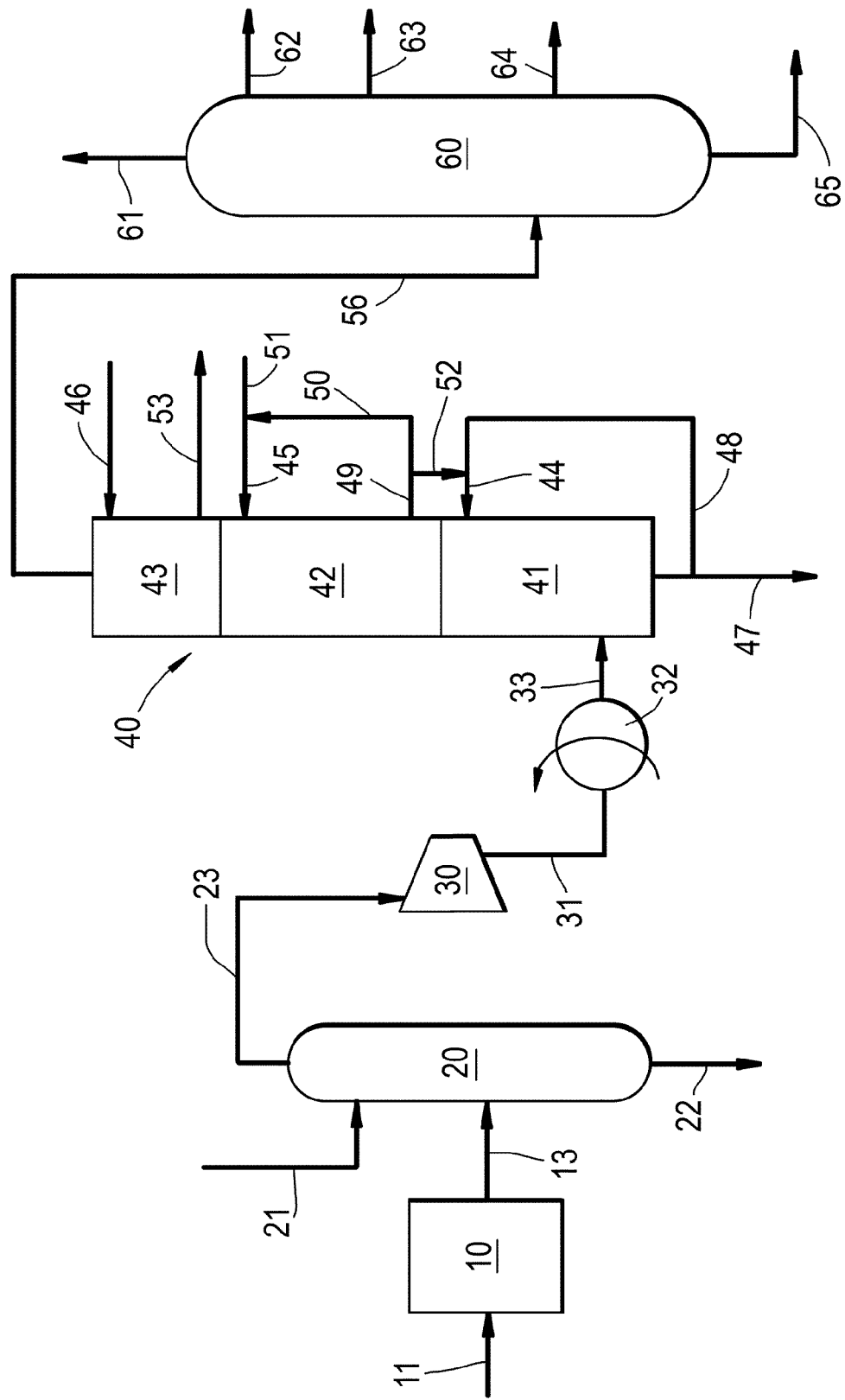

PROCESS FOR THE PREPARATION OF AN OLEFINIC PRODUCT FROM AN OXYGENATE

Priority Claim

The present application is the National Stage (§371) of International Application No. PCT/EP2013/077996, filed Dec. 24, 2013, which claims priority from European Patent Application 12199591.4, filed Dec. 28, 2012 incorporated herein by reference.

FIELD OF THE INVENTION

The invention relates to a process for the preparation of an olefinic product comprising ethylene and/or propylene from an oxygenate.

BACKGROUND TO THE INVENTION

Conventionally, ethylene and propylene are produced via steam cracking of paraffinic feedstocks including ethane, propane, naphtha and hydrowax. An alternative route to ethylene and propylene is an oxygenate-to-olefin (OTO) process. Interest in OTO processes for producing ethylene and propylene is growing in view of the increasing availability of natural gas. Methane in the natural gas can be converted into for instance methanol or dimethylether (DME), both of which are suitable feedstocks for an OTO process.

In an OTO process, an oxygenate such as methanol, ethanol or dimethylether is provided to a reaction zone of a reactor comprising a suitable conversion catalyst and converted into ethylene and propylene. In addition to the desired ethylene and propylene, a substantial part of the oxygenate is converted into higher hydrocarbons including $C4^+$ olefins, paraffins and carbonaceous deposits on the catalyst. The effluent from the reactor comprising the olefins, any unconverted oxygenates, some oxygenate byproducts and other reaction products such as water may then be treated to provide separate component streams. In case of a water-soluble oxygenate in the feedstock, such as for example methanol or ethanol, the greater part of the unreacted oxygenates can be separated from the reaction effluent, for instance by contacting with a cooled aqueous stream in a quench tower.

In order to increase the ethylene and propylene yield of the process, the $C4^+$ olefins may be recycled to the reaction zone or alternatively further cracked in a dedicated olefin cracking zone to produce further ethylene and propylene.

Due to the high temperatures in the reaction zone and the acidity of the catalyst, a portion of the oxygenates such as methanol may unavoidably decompose thermally or catalytically into oxides of carbon, i.e. carbon monoxide and carbon dioxide in the gaseous form. The carbonaceous deposits on the catalyst can be removed by the periodic regeneration of the catalyst by heating it with an oxidising gas such as oxygen, in order to burn off the deposits.

Carbon dioxide generated during the OTO process is an acid gas which is thus present in the effluent from the reactor. In order to prevent contamination of the olefinic product and problems associated with the formation of solid carbon dioxide during the separation of the olefinic product into olefinic component streams, which may be carried out at cryogenic temperatures, carbon dioxide should be removed from the reaction effluent and from the gaseous effluent from the quench tower before separation into olefinic component streams. This is typically done by washing the gaseous effluent with a caustic solution in a caustic tower.

The gaseous effluent from the quench water tower in an OTO process typically still comprises small amounts of unconverted oxygenate and oxygenate byproduct. In case of a water-soluble oxygenate in the OTO feedstock, such as for example methanol or ethanol, the gaseous effluent comprises unconverted water-soluble oxygenate and some water-insoluble oxygenate byproduct, dimethylether in case methanol is used as feedstock and diethylether in case ethanol is used as feedstock. In case of a water-insoluble oxygenate in the feedstock, e.g. dimethylether or diethylether, typically water-soluble oxygenates are formed as byproduct (methanol in case of dimethylether as feedstock oxygenate and ethanol in case of diethylether as feedstock). Thus, the effluent of an OTO reactor and the gaseous effluent of a quench water tower in an OTO process comprise unconverted oxygenate and oxygenate byproduct of which at least the unconverted oxygenate or the oxygenate byproduct is a water-soluble oxygenate. Another source of water-soluble oxygenate in the gaseous olefinic stream in an OTO process may be the water-soluble oxygenate, typically methanol, that is often used for washing water-insoluble oxygenate (present as unconverted oxygenate or as oxygenate byproduct) from the quench water tower effluent in an OTO process. Dimethylether is typically present in such effluent as unconverted dimethylether in case of a feedstock comprising dimethylether or as byproduct in case of a feedstock comprising methanol.

Methanol or other water-soluble oxygenates in the gaseous quench tower effluent will not be removed by the wash treatment with a caustic solution in the caustic tower that is typically carried out to remove carbon dioxide and other acids. Since the presence of oxygenates in a propylene product that will be used for the manufacture of polypropylene will lead to undesired water production in the polypropylene manufacture, such oxygenates need to be removed from the OTO reaction effluent or from the propylene product stream recovered from such effluent. It is known to remove methanol or other water-soluble oxygenates by leading the propylene product stream over a guard bed prior to polypropylene manufacture. Alternatively, the water-soluble oxygenates are washed from the gaseous effluent from the quench tower by means of a water wash step upstream of the caustic tower.

SUMMARY OF THE INVENTION

It has now been found that by modifying the water wash step that is usually applied as final stage in a caustic tower treatment of a gaseous effluent from an oxygenate-to-olefins process, methanol or other water-soluble oxygenates can be removed from such effluent to an extent that no additional step for removal of such oxygenates from the effluent or from an olefin product stream recovered from such effluent is needed. In the process according to the invention, water that is essentially free of water-soluble oxygenate, such as for example boiler feed water or water of a similar quality, is used as wash water in a final water wash stage in the caustic tower that is used for removal of acids from a gaseous olefinic effluent from an oxygenate-to-olefins process. The water wash stage is carried out as a once-through water wash, i.e. without recycling used wash water to the water wash stage or to another stage in the caustic tower.

Accordingly, the present invention provides a process for the preparation of an olefinic product comprising ethylene and/or propylene from an oxygenate, the process comprising the following steps:

a) contacting an oxygenate feedstock in an oxygenate conversion reaction zone with a molecular sieve-comprising catalyst at a temperature in the range of from 350 to 1000° C. to produce an oxygenate conversion effluent comprising olefins, water, carbon dioxide, unconverted oxygenate and oxygenate byproduct, wherein the unconverted oxygenate or the oxygenate byproduct is a water-soluble oxygenate;

b) separating water from the oxygenate conversion effluent to obtain a water-depleted gaseous oxygenate conversion effluent comprising olefins, carbon dioxide, unconverted oxygenate and oxygenate byproduct;

c) compressing the water-depleted gaseous effluent with the optional removal of any condensed phase to obtain a compressed water-depleted gaseous stream comprising olefins and carbon dioxide;

d) treating the compressed gaseous stream in a caustic tower, wherein the compressed gaseous stream is first countercurrently contacted with a caustic solution in one or more stages in series and is then countercurrently washed with a water stream in a final stage to obtain a washed gaseous stream comprising olefins; and e) subjecting the washed gaseous stream to one or more separation steps such that at least an olefin product stream comprising ethylene and/or propylene is obtained, wherein, in the final stage of the caustic tower, the water stream is a water stream that is essentially free of water-soluble oxygenate and a spent water stream comprising caustic and water-soluble oxygenate is obtained, which spent water stream is withdrawn from the process.

An important advantage of the process according to the invention is that use is made of a water wash step that is typically present in a process for the preparation of an olefinic product from an oxygenate. This known water wash step is typically required to prevent any carryover of caustic to a next process step. By modifying the known water wash step in the caustic tower, additional steps for removal of methanol or other water-soluble oxygenates are not needed.

BRIEF DESCRIPTION OF THE DRAWING

The Figure schematically shows a line-up of the process according to the invention.

DETAILED DESCRIPTION OF THE INVENTION

In the process according to the invention, an olefinic product comprising ethylene and/or propylene is prepared by first converting an oxygenate into olefins in a so-called oxygenate conversion step (step a)) to produce an oxygenate conversion effluent comprising olefins, water, carbon dioxide, unconverted oxygenate and oxygenate byproduct, wherein the unconverted oxygenate or the oxygenate byproduct is a water-soluble oxygenate. Typically, the oxygenate byproduct is water-insoluble in case of a water-soluble unconverted oxygenate and vice versa. In step b), water is separated from the oxygenate conversion effluent to obtain a water-depleted gaseous oxygenate conversion effluent comprising olefins, carbon dioxide and still some unconverted oxygenate and oxygenate byproduct. In subsequent step c), the water-depleted gaseous effluent obtained in step b) is compressed to obtain a compressed gaseous stream comprising olefins and carbon dioxide.

In step d), carbon dioxide and other acids are separated from the compressed gaseous stream by subjecting the compressed gaseous stream to a caustic wash treatment, wherein the gaseous stream is countercurrently contacted with a caustic solution in one or more stages in series in a caustic tower. In a final stage in the caustic tower, the gaseous effluent is countercurrently washed with a water stream that is essentially free of water-soluble oxygenate. A spent water stream comprising caustic and water-soluble oxygenate is obtained in the final stage of the caustic tower and is withdrawn from the process, i.e. not recycled to the final stage or to any other stage of the caustic tower. In step d), a washed gaseous stream comprising olefins is obtained. This stream is subjected in step e) to one or more separation steps to obtain at least an olefin product stream comprising ethylene and/or propylene.

The process preferably comprises a further step f), wherein the water-depleted gaseous oxygenate conversion effluent obtained in step b) or the compressed water-depleted gaseous stream obtained in step c) is washed with a water-soluble oxygenate in order to remove any water-insoluble oxygenate that is present as unconverted feedstock oxygenate or as oxygenate byproduct. A gaseous stream that is depleted in water-insoluble oxygenate, preferably is essentially free of water-insoluble oxygenate, is obtained in step f). The gaseous stream obtained in step f) is either compressed in step c) or, in case step f) is carried out on the already compressed gaseous stream obtained in step c), is supplied to the caustic tower in step d). As a result of wash step f), the gaseous stream depleted in water-insoluble oxygenate will comprise additional water-soluble oxygenate. Preferably the gaseous stream that is washed in step f) comprises dimethylether as water-insoluble oxygenate and methanol is as the water-soluble oxygenate for washing this stream.

In oxygenate conversion step a), an oxygenate is converted into lower olefins, i.e. ethylene and propylene, by contacting an oxygenate feedstock comprising the oxygenate with a molecular sieve-comprising catalyst at a temperature in the range of from 350 to 1000° C.

Reference herein to an oxygenate is to a compound comprising at least one alkyl group that is covalently linked to an oxygen atom. The oxygenate preferably is an oxygenate wherein the at least one alkyl group has up to five carbon atoms, more preferably up to four, even more preferably one or two carbon atoms, most preferably is methyl. Monoalcohols and dialkylethers are particularly suitable oxygenates. Methanol, dimethylether and mixtures thereof are examples of particularly preferred oxygenates. Most preferably, the oxygenate is methanol.

The oxygenate feedstock preferably comprises methanol, more preferably comprises at least 80 wt % methanol, even more preferably at least at 90 wt % methanol, even more preferably at least 95 least wt % methanol. An oxygenate feedstock essentially consisting of methanol is particularly preferred. Reference herein to 'essentially consisting of a component' is to a stream that does not comprise other components apart from small amounts of contaminants. Preferably, such stream will comprises at least 99 wt % of the such component.

Oxygenate conversion step a) is carried out by contacting the oxygenate with a molecular sieve-comprising catalyst at a temperature in the range of from 350 to 1000° C., preferably of from 350 to 750° C., more preferably of from 450 to 700° C., even more preferably of from 500 to 650° C. The conversion may be carried out at any suitable pressure, preferably at a pressure in the range of from 1 bar to 50 bar (absolute), more preferably of from 1 bar to 15 bar (absolute). A pressure in the range of from 1.5 to 4.0 bar (absolute) is particularly preferred.

Any molecular sieve comprising catalyst known to be suitable for the conversion of oxygenates, in particular alkanols and dialkylethers, into lower olefins may be used. Preferably the catalyst comprises a molecular sieve having a 8-, 10- or 12-ring structure and an average pore size in the range of from 3Å to 15Å. Examples of suitable molecular sieves are silicoaluminophosphates (SAPOs), aluminophosphates (AlPO), metal-substituted aluminophosphates or metal-substituted silicoaluminophosphates. Preferred SAPOs include SAPO-5, -8, -11, -17, -18, -20, -31, -34, -35, -36, -37, -40, -41, -42, -44, -47 and -56. SAPO-17, -18, -34, -35, and -44 are particularly preferred.

A particular suitable class of molecular sieves are zeolites, more in particular a zeolite with a 10-membered ring structure. Zeolite-comprising catalysts are known for their ability to convert higher olefins into lower olefins, in particular to convert $C4^+$ olefins into ethylene and/or propylene. Suitable zeolite-comprising catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48. Preferably, the catalyst comprises at least one zeolite selected from MFI, MEL, TON and MTT type zeolites, more preferably at least one of ZSM-5, ZSM-11, ZSM-22 and ZSM-23 zeolites.

The zeolite in the oxygenate conversion catalyst is preferably predominantly in the hydrogen form. Preferably at least 50 wt %, more preferably at least 90 wt %, even more preferably at least 95 wt %, still more preferably at least 100 wt % of the zeolite is in the hydrogen form.

The molecular sieve-comprising catalyst may further comprise a binder material such as for example silica, alumina, silica-alumina, titania, or zirconia, a matrix material such as for example a clay, and/or a filler.

Besides lower olefins, $C4^+$ hydrocarbons including $C4^+$ paraffins, $C4^+$ olefin, and aromatic hydrocarbons like benzene, toluene and C8 aromatics, such as xylenes and ethylbenzene, are formed as by-product. Thus, an oxygenate conversion effluent comprising ethylene, propylene and $C4^+$ hydrocarbons is produced in step a).

In oxygenate conversion step a), not only lower olefins and $C4^+$ hydrocarbons, but also water and oxygenate byproduct (typically alcohol in case of an ether as feedstock oxygenate and ether in case of an alcohol as feedstock oxygenate) are formed. In step b), water is separated from the gaseous oxygenate conversion effluent. Such separation step is well-known in the art and typically comprises passing the effluent to a separation zone, such as a gas/liquid contactor, preferably a column comprising packing and/or trays also known as quench water tower, wherein the gaseous effluent is contacted with an aqueous stream, typically water. The aqueous stream can condense water and higher hydrocarbons, typically $C7^+$ hydrocarbons, from the gaseous effluent and typically absorbs part of any unreacted water-soluble oxygenate. Thus, a water-depleted gaseous oxygenate conversion effluent comprising olefins and further comprising carbon dioxide, unconverted oxygenate and oxygenate byproduct, is obtained.

In step c), the water-depleted gaseous effluent obtained in step b) is compressed. This may be done in any suitable compressor. The compressor may be a single stage or a multi-stage compressor. Preferably, a multi-stage centrifugal compressor is used. The water-depleted gaseous effluent is preferably compressed to a pressure of at least 5 bar (absolute), more preferably at least 9 bar (absolute). Preferably, the water-depleted gaseous effluent is compressed to a pressure of at most 45 bar, more preferably at most 20 bar (absolute). Any condensed phase such as water and condensed $C5^+$ hydrocarbons may be removed from the compressed stream, for example by means of one or more gas-liquid separators, such as for example knock-out drums. In a multi-stage compression step, condensed phase may be removed after each compression stage. In the process according to the invention, the gaseous stream comprising olefins may be further compressed after caustic wash treatment step d). It will be appreciated that the pressure to which the stream is compressed in step c), i.e. prior to the caustic treatment step d), will inter alia depend on whether there is a further compression step provided for the washed gaseous stream, i.e. between caustic treatment step d) and separation step e).

In step c) is thus obtained a compressed gaseous stream comprising olefins and carbon dioxide.

Preferably, a wash step for removal of water-insoluble oxygenate (step f)) is carried out between water quench step b) and compression step c) or between compression step c) and caustic treatment step d). Such wash step f) has been described hereinabove.

In step d), the compressed water-depleted gaseous stream obtained in step c), optionally after removal of water-insoluble oxygenate from this stream, is subjected to a caustic wash treatment in a caustic tower in order to separate carbon dioxide or other acids from the compressed gaseous stream. Caustic wash treatments for removal of acid gases are well known in the art. In such treatment, the gaseous stream to be treated is countercurrently contacted with a caustic solution, and, in a final stage, with a water stream, to obtain a washed gaseous stream.

Any known process conditions and tower configurations for caustic treatments for acid gas removal may suitably be used in the process according to the invention. Preferably, the gaseous stream is countercurrently contacted with a caustic solution in at least two stages in series, more preferably in two or three stages, most preferably in two stages. In case of at least two stages, the gaseous stream is contacted in each stage with a caustic solution having a concentration of caustic, wherein the concentration of caustic in a next stage is higher than the concentration of caustic in the stage directly preceding said next stage. Thus, the concentration of the caustic solution in the second stage is higher than the concentration of the caustic solution in the first stage. Reference herein to the first stage is to the first stage with regard to the direction of flow of the gaseous stream to be treated. Thus, the first stage is the lowest stage, i.e. the stage wherein the gaseous stream is entering the caustic tower.

The caustic solution is an aqueous alkaline stream suitable to absorb acid gases. Such caustic solutions are known in the art. Any suitable caustic solution may be used, preferably a solution of an alkali metal hydroxide such a sodium hydroxide or potassium hydroxide. The caustic solution may have any suitable concentration of caustic, preferably in the range of from 0.5 to 2.5 moles of hydroxide ions per litre (equivalent to 2 to 10 wt % sodium hydroxide based on the weight of water). In case of two caustic stages, the concentration of the caustic solution in the first stage is preferably in the range of from 0.5 to 1.0 moles of hydroxide ions per litre (equivalent to 2 to 4 wt % sodium hydroxide); in the second stage in the range of from 1.25 to 2.5 moles of hydroxide ions per litre (equivalent to 5 to 10 wt % sodium hydroxide).

In a final stage, the gaseous stream is countercurrently washed with a water stream in order to remove any remaining caustic from the gaseous stream. Typically, each of the caustic stages and the water wash stage are carried out in separate sections of the tower. In each section, liquid extractant (caustic solution or water stream) is supplied to the top of the section and discharged from the bottom of the section. The gaseous stream is supplied to the bottom of each section and withdrawn via the top to the next section or to a work-up section. Fresh caustic solution is typically supplied to the most concentrated solution, i.e. to the last caustic section. Caustic solution withdrawn from the bottom of a section is partially recycled to the top of that section and partially supplied to the top of the preceding section as make-up of the losses of caustic (e.g. sodium hydroxide) as a result of the reaction of the caustic with carbon dioxide and other acids. Caustic solution withdrawn from the bottom of the first section is partially recycled to the top of the first section and partially withdrawn from the caustic tower as spent caustic.

In order to remove not only caustic but also any water-soluble oxygenate present in the gaseous stream, a water stream that is essentially free of water-soluble oxygenate is countercurrently contacted with the gaseous stream in the final stage of the caustic tower, i.e. the water wash stage. Thus, a spent water stream comprising caustic and water-soluble oxygenate is obtained. The spent water stream is withdrawn from the process. The spent water stream is thus once led through the water wash section (final stage) of the caustic tower and not recycled to the water wash section to form part of the water stream or to any other section of the caustic tower. The water stream used in the final stage preferably is an external water stream, i.e. a water stream from an external source and not a water stream that is recycled within the process according to the invention.

The water stream may be any suitable water stream that is essentially free of water-soluble oxygenate and preferably also essentially free of carbon dioxide. Reference herein to 'essentially free of a component' is to a stream comprising less than 0.1 wt %, preferably less than 0.05 wt %, more preferably less than 0.01 wt % of such component. Boiler feed water is an example of a suitable water stream.

The operating temperature in the caustic tower may be any suitable temperature. Preferably, the operating temperature is at most 50° C., more preferably in the range of from 35 to 45° C. The pressure may be any pressure known to be suitable for a caustic wash treatment, preferably in the range of from 9 to 45 bar, more preferably of from 10 to 20 bar (absolute).

Preferably, the compressed gaseous stream to be treated in step d) is superheated before entering the caustic tower in order to avoid undesired condensation of hydrocarbons in the caustic tower. More preferably, the compressed gaseous stream is heated to a temperature in the range of from 2 to 5° C. above its dew point prior to subjecting the compressed gaseous stream to the caustic wash treatment in step d). Preferably, the temperature of the compressed gaseous stream that is contacted with the caustic solution is at most 40° C.

In the process according to the invention, there is no need to include a separate water wash step for removal of methanol or other water-soluble oxygenates upstream of the caustic tower and downstream of water quench step b). In known oxygenate-to-olefins processes, it is usual to include a water wash step, in particular after a methanol wash step for dimethylether removal. The process according to the invention preferably does not comprise washing the gaseous stream with water upstream of step d) and downstream of step b). Even in case wash step f) is applied, such water wash step between steps f) and d) is not needed, since any water-soluble oxygenate present can be removed in the water wash section (final stage) of the caustic tower.

In separation or work-up step e), the washed gaseous stream comprising olefins obtained in step d) is subjected to one or more separation steps to obtain at least an olefin product stream comprising ethylene and/or propylene. In this step, the washed gaseous stream is typically first dried and then separated into different fractions by means known in the art. Preferably, a fraction comprising mainly ethylene is first separated from the washed gaseous stream in a de-ethaniser and a fraction mainly comprising propylene is separated from the bottoms of the de-ethaniser in a de-propaniser. The bottoms of the de-propaniser contain $C4^+$ hydrocarbons. Alternatively, a fraction comprising both ethylene and propylene may be separated from the washed gaseous stream to obtain an olefinic product stream comprising both ethylene and propylene.

The $C4^+$ hydrocarbon fraction obtained as bottoms of a de-propaniser is preferably further separated into a fraction comprising $C5^+$ hydrocarbons and a fraction comprising C4 hydrocarbons, mainly C4 olefins, in for example a de-butaniser. The fraction comprising C4 hydrocarbons may be recycled to step a) to convert C4 olefins into additional ethylene and propylene.

At the bottom of the caustic tower, a liquid phase comprising spent caustic solution is present. Part of this liquid phase is typically recycled to the tower, in case of a tower with more than one section to the top of the first section, and part of this liquid phase is discharged as spent caustic solution from the tower.

DETAILED DESCRIPTION OF THE DRAWING

In the Figure is schematically shown a line-up of the process according to the invention. Methanol is supplied to oxygenate conversion reaction zone 10 via conduit 11 and converted into an oxygenate conversion effluent comprising olefins, water, carbon dioxide, unconverted methanol and some dimethylether. The effluent is supplied via conduit 13 to quench tower 20 wherein it is contacted with water that is supplied via conduit 21, to provide a stream 22 comprising water and a water-depleted gaseous olefinic stream. The water-depleted gaseous olefinic stream is supplied via line 23 to compression zone 30 to provide a compressed water-depleted gaseous stream. The compressed gaseous stream is supplied via conduit 31 to superheater 32 to provide a superheated compressed gaseous stream which is then supplied via conduit 33 to caustic tower 40 to be countercurrently extracted with sodium hydroxide. Caustic tower 40 has two sections 41, 42 for caustic treatment and water wash section 43. The superheated compressed gaseous stream is supplied via conduit 33 to the lower part of first section 41 and countercurrently contacted in section 41 with 2 wt % sodium hydroxide that is supplied to the top of section 41 via conduit 44. In second section 42, the gaseous stream is countercurrently contacted with 10 wt % sodium hydroxide that is supplied to the top of section 42 via conduit 45. In final section 43, the gaseous stream is contacted with boiler feed water supplied via conduit 46.

Spent liquid phase is withdrawn from the bottom of section 41 via conduit 47 and partially recycled to section 41 via conduit 48. Used caustic is withdrawn from section 42 via conduit 49 and partly recycled to section 42 via conduit 50 to form, together with fresh caustic solution supplied via conduit 51, the caustic solution supplied to section 42. Part of the used caustic withdrawn from section 42 is supplied to preceding section 41 via line 52. Spent water comprising caustic and methanol is withdrawn from the bottom of section 43 via conduit 53 and entirely withdrawn from the process.

Washed gaseous stream is withdrawn from caustic tower 40 via conduit 56 and supplied to work-up section 60. In work-up section 60, the washed gaseous stream is separated into a light gas stream, an ethylene stream, a propylene stream, a C4 hydrocarbon fraction and a C5$^+$ hydrocarbon fraction, which are withdrawn from section 60 via lines 61, 62, 63, 64 and 65, respectively. Part of the C4 hydrocarbon fraction may be recycled to oxygenate conversion zone 10 for conversion of any olefins therein into lower olefins (not shown).

That which is claimed is:

1. A process for the preparation of an olefinic product comprising ethylene and/or propylene from an oxygenate, the process comprising the following steps:
    a) contacting an oxygenate feedstock in an oxygenate conversion reaction zone with a molecular sieve-comprising catalyst at a temperature in the range of from 350 to 1000° C. to produce an oxygenate conversion effluent comprising olefins, water, carbon dioxide, unconverted oxygenate and oxygenate byproduct, wherein the unconverted oxygenate or the oxygenate byproduct is a water-soluble oxygenate;
    b) separating water from the oxygenate conversion effluent to obtain a water-depleted gaseous oxygenate conversion effluent comprising olefins, carbon dioxide, unconverted oxygenate and oxygenate byproduct;
    c) compressing the water-depleted gaseous effluent with the optional removal of any condensed phase to obtain a compressed water-depleted gaseous stream comprising olefins and carbon dioxide;
    d) treating the compressed gaseous stream in a caustic tower, wherein the compressed gaseous stream is first countercurrently contacted with a caustic solution in one or more stages in series and is then countercurrently washed with a water stream in a final stage to obtain a washed gaseous stream comprising olefins; and
    e) subjecting the washed gaseous stream to one or more separation steps such that at least an olefin product stream comprising ethylene and/or propylene is obtained, wherein, in the final stage of the caustic tower, the water stream is a water stream that is essentially free of water-soluble oxygenate and a spent water stream comprising caustic and water-soluble oxygenate is obtained, which spent water stream is withdrawn from the process in the final stage.

2. A process according claim 1, wherein the unconverted oxygenate or the oxygenate byproduct in the oxygenate conversion effluent is a water-insoluble oxygenate and the process further comprises the following step:
    f) washing the water-depleted gaseous effluent or the compressed water-depleted gaseous stream with a water-soluble oxygenate to obtain a gaseous stream depleted in the water-insoluble oxygenate, the gaseous stream comprising olefins, carbon dioxide, and the water-soluble oxygenate used for washing.

3. A process according to claim 2, wherein the water-insoluble oxygenate is dimethylether and the water-soluble oxygenate used for washing is methanol.

4. A process according to claim 1, wherein the oxygenate feedstock comprises methanol.

5. A process according to claim 4, wherein the oxygenate feedstock consists essentially of methanol.

6. A process according to claim 1, wherein the oxygenate feedstock comprises dimethylether.

7. A process according to claim 1, wherein the water stream that is essentially free of water-soluble oxygenate is an external water stream.

8. A process according to claim 1, wherein the water stream that is essentially free of water-soluble oxygenate is boiler feed water.

9. A process according to claim 1, wherein the process does not comprise washing the gaseous stream with water upstream of the caustic tower.

* * * * *